US012600933B2

(12) United States Patent
Duckert et al.

(10) Patent No.: US 12,600,933 B2
(45) Date of Patent: Apr. 14, 2026

(54) CONTROL OF CELL ELECTROPORATION

(71) Applicants: IMEC VZW, Leuven (BE); Katholieke Universiteit Leuven, KU LEUVEN R&D, Leuven (BE)

(72) Inventors: Bastien Duckert, Heverlee (BE); Dries Braeken, Leuven (BE); Maarten Fauvart, Bertem (BE)

(73) Assignees: IMEC VZW, Leuven (BE); Katholieke University Leuven, KU LEUVEN R&D, Leuven (BE)

( * ) Notice: Subject to any disclaimer, the term of this patent is extended or adjusted under 35 U.S.C. 154(b) by 752 days.

(21) Appl. No.: 17/326,897

(22) Filed: May 21, 2021

(65) Prior Publication Data

US 2021/0371796 A1     Dec. 2, 2021

(30) Foreign Application Priority Data

May 29, 2020     (EP) ..................................... 20177283

(51) Int. Cl.
| | |
|---|---|
| *C12M 1/42* | (2006.01) |
| *C12N 13/00* | (2006.01) |
| *G01N 33/483* | (2006.01) |

(52) U.S. Cl.
CPC ............. *C12M 35/02* (2013.01); *C12N 13/00* (2013.01); *G01N 33/4836* (2013.01)

(58) Field of Classification Search
None
See application file for complete search history.

(56) References Cited

U.S. PATENT DOCUMENTS

| | | | |
|---|---|---|---|
| 11,609,223 B2 * | 3/2023 | Lopez ..................... | H03F 3/393 |
| 2005/0282284 A1 * | 12/2005 | Rubinsky ............... | A61N 1/327 |
| | | | 435/459 |

(Continued)

FOREIGN PATENT DOCUMENTS

| | | | |
|---|---|---|---|
| WO | 01/81532 A1 | 11/2001 | |
| WO | WO-2006017762 A2 * | 2/2006 | ......... G01N 33/4836 |

(Continued)

OTHER PUBLICATIONS

Lopez, et al. "A Multimodal CMOS MEA for High-Throughput Intracellular Action Potential Measurements and Impedance Spectroscopy in Drug-Screening Applications". IEEE Journal of Solid-State Circuits, vol. 53, No. 11, Nov. 2018 (Year: 2018).*

(Continued)

*Primary Examiner* — Michael A Marcheschi
*Assistant Examiner* — Nathan G Esperon
(74) *Attorney, Agent, or Firm* — McDonnell Boehnen Hulbert & Berghoff LLP

(57) ABSTRACT

An electrode unit for performing electroporation of a biological cell is provided, including at least one electrode which can contact a cell. A stimulation unit and an impedance measurement device are connected to the cell, respectively to provide signals to provide cell electroporation and to measure the impedance of the electrode in contact with the cell. Further, a memory stores a predetermined value of an impedance parameter of the biological cell, and it is arranged to be readable by a comparing element. The comparing element is configured to compare the value stored in the memory with a value measured with the impedance measurement device, and to produce an adjustment signal to the stimulation unit, forming a feedback loop. The unit is further configured to apply a further electrical (Continued)

signal for providing electroporation of the cell upon receiving the adjustment signal from the comparing element.

19 Claims, 5 Drawing Sheets

(56) References Cited

U.S. PATENT DOCUMENTS

| | | | |
|---|---|---|---|
| 2018/0036529 A1 | 2/2018 | Jaroszeski et al. | |
| 2019/0117964 A1* | 4/2019 | Bahrami | A61N 1/327 |

FOREIGN PATENT DOCUMENTS

| | | | | |
|---|---|---|---|---|
| WO | WO-2006058185 A2 * | 6/2006 | | C12M 35/02 |
| WO | 2006/112870 A1 | 10/2006 | | |
| WO | WO-2018234238 A1 * | 12/2018 | | C12M 35/02 |

OTHER PUBLICATIONS

Extended European Search Report and Written Opinion, Application No. EP20177283.7, mailed Oct. 29, 2021, 8 pages.

Guo, Xiaoliang, and Rong Zhu. "Controllable in-situ cell electroporation with cell positioning and impedance monitoring using micro electrode array." Scientific reports 6, No. 1 (2016): 1-8.

Lopez, Carolina Mora, Ho Sung Chun, Laurent Berti, Shiwei Wang, Jan Putzeys, Carl Van Den Bulcke, Jan-Willem Weijers et al. "A 16384-electrode 1024-channel multimodal CMOS MEA for high-throughput intracellular action potential measurements and impedance spectroscopy in drug-screening applications." In 2018 IEEE International Solid-State Circuits Conference—(ISSCC), pp. 464-466. IEEE, 2018.

* cited by examiner

CONTROL OF CELL ELECTROPORATION

CROSS-REFERENCE TO RELATED APPLICATIONS

The present application is a non-provisional patent application claiming priority to European Patent Application No. 20177283.7, filed on May 29, 2020, the contents of which are hereby incorporated by reference.

FIELD OF THE DISCLOSURE

The present disclosure relates to devices for and methods of cell electroporation, which can be used in transfection. More in particular, it relates to electroporation of individual cells in contact with electrodes.

BACKGROUND

Electroporation is an approach widely used for introducing nucleic acids and proteins directly into cells, a process called transfection. By applying an electrical signal, e.g. electrical pulses, transient pores form in the lipid plasma membrane that envelops the cell, allowing a temporary exchange of molecules with the extracellular environment. Because it relies on physical membrane disruption, electroporation is universal both in type of cargo that can be delivered, as well as in cell type that can be targeted. In addition, it is generally efficient and safe to perform, thanks to the availability of specialized commercial equipment. Those devices usually make use of a large cuvette containing millions of cells in suspension, across which a large electrical potential is applied.

A disadvantage of the conventional method stems from the cytotoxicity caused by irreversible pore formation upon overexposure. Other disadvantages are the relatively limited spatiotemporal control and limited dosage control. This can partly be explained by electroporation typically being carried out in bulk, with millions of cells trapped between two electrodes, and therefore subjected to locally varying electroporation parameters. This variation is usually caused by variations in distance between cell and electrode, and also due to cell-to-cell variation between primary cell types.

In order to improve spatiotemporal control, before electroporation, cells may be provided on a surface comprising electrodes, for example a microelectrode array (MEA). Guo, X., & Zhu, R. (2016), "Controllable in-situ cell electroporation with cell positioning and impedance monitoring using micro electrode array," Scientific reports, 6,31392, discloses an example of electroporation dynamics on an MEA. Additionally, it discloses an example of use of impedance measurements to monitor single-cell recovery after EP.

It would be desirable to provide good cell electroporation, allowing transfection thereof, with high efficiency and preferably low cytotoxicity, on a microelectrode array platform.

SUMMARY

The disclosure provides a method and a device for providing and ensuring electroporation with reduced rate of cell death or without cell death. The disclosure provides a unit and a method including the possibility of introducing feedback so adjustment of electroporation parameters is possible before and even during electroporation.

In a first aspect, the present disclosure provides an electrode unit for performing electroporation of a biological cell. The electrode unit comprises at least one electrode configured to form contact with the cell, for providing an electrical pulse to the cell and for measuring an impedance of the electrode and the cell. A stimulation unit is electrically connected to the electrode, and an impedance measurement device is configured to measure the impedance of the electrode in contact with the cell when present. Further, a memory stores a predetermined value of an impedance parameter of the biological cell, and it is arranged to be readable by a comparing element.

The comparing element is configured to compare the value stored in the memory with a value measured with the impedance measurement device, and to produce an adjustment signal for adjusting the electroporation process based on the result of the comparison if the result is different exceeding a predetermined threshold. The electrode unit is configured to provide the signal from the comparing element to the stimulation unit, thereby forming a feedback loop. The stimulation unit is configured to apply, via the electrode, an electrical signal to the cell, such that the parameters defining the signal are adapted to produce electroporation. It is further configured to apply a further electrical signal for providing electroporation of the cell upon receiving the adjustment signal from the comparing element.

An EP and impedance measurement can be combined in an electrode unit which provides electroporation. The unit provides adjustment of electroporation parameters, possibly yielding electroporation with reduced rate of cell death or without cell death.

The electrode unit is configured to provide a signal such that an impedance value can be measured without electroporation. Cell attachment can be checked before electroporation, for example, at a single-cell level.

In some embodiments of the present disclosure, the memory stores a predetermined threshold impedance value ($\theta A$), and further, the comparing element is configured to provide an initial adjustment signal if the initial impedance values, measured without electroporation, do not reach this predetermined threshold impedance value $\theta A$. The stimulation unit is configured to adapt the parameters of the electrical signal (the one that provides electroporation) so as to apply a stronger electrical signal than the electrical signal with predetermined parameters for that cell upon receiving the initial adjustment signal.

Electroporation of the cell can be improved even in the cases where the attachment of the cell to the electrode is suboptimal.

In some embodiments of the present disclosure, the memory stores a threshold impedance drop value ($\theta$). Further, the comparing element is configured to provide an adjustment signal when the impedance values measured by the measurement device show an impedance drop value which does not reach the stored threshold impedance drop value ($\theta$).

The electroporation process can be corrected in case there is failure to provide electroporation, even in cases where the constant impedance value shows good attachment.

In particular embodiments, the stimulation unit is adapted to apply a further electrical signal upon receiving an adjustment signal from the comparing element. The further signal may being stronger than, weaker than, or the same as, the previous electrical signal that caused the generation of the adjustment signal. This choice is made based on the measured impedance drop value produced by that previous electrical signal, for providing electroporation of that cell. For example, a decision element (implemented in a physical element or as software) may make the choice.

The electroporation process can be corrected while at the same time correcting the parameters of the stimulating EP signal in case there is failure to provide electroporation.

In some embodiments of the present disclosure, the comparing element is configured to provide the adjustment signal as soon as the impedance values measured by the measurement device show an impedance drop value which does not reach the threshold impedance drop value stored in the memory. Further, the stimulation unit is configured to apply the electrical signal as soon as the adjustment signal from the comparing element is received.

The correction can be performed as soon as the failure is detected, thereby increasing the speed of the process.

In some embodiments of the present disclosure, the stimulation unit can be re-configured to set at least one parameter of the electrical signal to a lower value for providing an electrical signal with lower energy than the signal with predetermined parameters, if the impedance measurement device does not detect an increase of impedance after applying an electrical signal for producing electroporation of a cell. This sets the parameters of the EP signal in following experiments (for a type of cell) to provide less energy in case an experiment (for that type of cell) resulted in cell death.

The standardized pulse for a type of cell can be corrected if no recovery, and hence cell death, is detected for that type of cell. In some embodiments, the pulse parameter causing cell death can be taken into account for further adjustments. For example in the case the subsequent pulse is not long or powerful enough to provide electroporation, the pulse length and/or power generally should not be adjusted to a values so high that again causes death.

In some embodiments of the present disclosure the electrode is a microelectrode. Single cell control can be provided.

In some embodiments of the present disclosure, the unit comprises an electrode array. A MEA combining EP and impedance measurement can be provided, for control of EP and optionally transfection for a plurality, e.g. thousands, of cells simultaneously, and allowing single-cell addressability.

In a further aspect, the present disclosure provides a cell interfacing device comprising the unit of the present disclosure. In some embodiments the cell interfacing device comprises hardware and/or software to control the electrodes, e.g. a MEA, which may be included in a chip, e.g. a disposable chip. The stimulation unit, comparators, etc. as well as control software may be implemented in a programmable cell interfacing device. In some embodiments, it may comprise fluidic units or elements, e.g. microfluidic units or elements, for providing cells on the electrodes, e.g. on the chip.

In a further aspect, the present disclosure provides a method for the electroporation of a biological cell. The method includes the steps of placing the cell on an electrode, applying a first electrical signal to the cell via the electrode to produce electroporation, measuring the impedance drop value of the electrode in contact with the cell, comparing the measured impedance value or drop value with a predetermined value of impedance drop of the biological cell, and applying a further electrical signal to the cell via the electrode to produce electroporation when the comparison results in a difference of more than a predetermined threshold. The further electrical signal may be stronger than, weaker than, or have the same strength as the precedent electrical signal for that cell when the measured impedance drop value is lower than the predetermined threshold impedance drop value, also called threshold drop value.

EP and impedance measurement can be combined with a feedback loop which provides adjustment of electroporation parameters, possibly yielding electroporation with reduced or without cell death. The further signal can be adapted depending on how close the measured drop value was to the threshold drop value, protecting the cell. If it was close to the threshold, the applied pulse may be e.g. slightly weaker.

In some embodiments of the present disclosure, the method further comprises measuring the (initial) impedance value of the electrode in contact with the cell before applying a first electrical signal. Applying a further electrical signal comprises adapting the predetermined parameters of the electrical signal for that cell when this initial measured impedance is lower than the predetermined threshold impedance value ($\theta A$), so that applying a first electrical signal comprises applying a stronger electrical signal than the predetermined electrical signal. Thus, the method can be dynamically adapted in case the cell contact is poor.

In some embodiments of the present disclosure the method comprises repeating the steps of measuring the impedance value of the electrode in contact with the cell, subsequently comparing the measured impedance drop value with a predetermined drop value of an impedance parameter of the biological cell and subsequently applying a further electrical signal for providing electroporation when the comparison results in a difference of more than a predetermined threshold. This feedback loop allows dynamic control and correction of the parameters, for example, in small steps, thus potentially improving adaptability of the method and protection of the cell, thus possibly yielding transfection and reducing the chances of cell death.

In some embodiments of the present disclosure the method comprises reconfiguring the predetermined parameters of the electrical signal for providing electroporation so that the electrical signal is weaker for that cell. This can be done when the impedance measurement device does not detect an increase of impedance (thus signalizing cell death) after applying a pulse for producing electroporation of a cell.

Particular aspects of the disclosure are set out in the accompanying independent and dependent claims. Features from the dependent claims may be combined with features of the independent claims and with features of other dependent claims as appropriate and not merely as explicitly set out in the claims.

The above and other characteristics and features of the present disclosure will become apparent from the following detailed description, taken in conjunction with the accompanying drawings, which illustrate, by way of example, the principles of the disclosure. This description is given for the sake of example only, without limiting the scope of the disclosure. The reference figures quoted below refer to the attached drawings.

BRIEF DESCRIPTION OF THE FIGURES

The above, as well as additional, features will be better understood through the following illustrative and non-limiting detailed description of example embodiments, with reference to the appended drawings.

Figure 1:
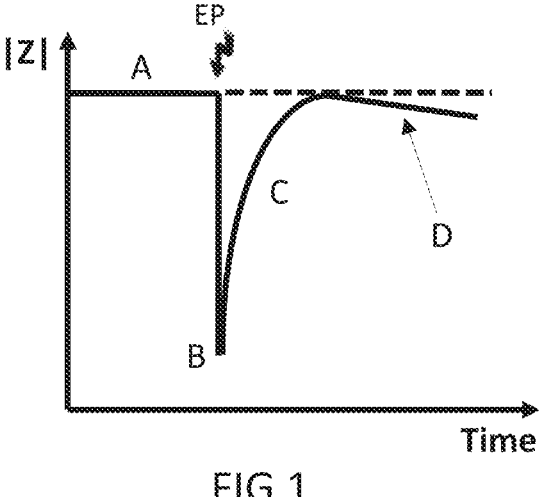
FIG. 1 is a graph of impedance as a function of time for a cell on an electrode showing four different stages of impedance monitoring during electroporation and successful transfection, according to an example.

The drawings are only schematic and are non-limiting. In the drawings, the size of some of the elements may be exaggerated and not drawn to scale for illustrative purposes.

Any reference signs in the claims shall not be construed as limiting in scope. In the different figures, the same reference signs refer to the same or analogous elements.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

Reference throughout this specification to "one embodiment" or "an embodiment" means that a particular feature, structure, or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the disclosure.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

In the following, signals may have electric character. When reference is made to an "electrical signal," reference is made to a signal for providing electroporation, and often will be referred to as "EP signals." These signals are provided in order to stimulate a cell on an electrode. On the other hand, "adjustment signals" may have also electric character, but these are used internally by a device in order to trigger an effect (such as adjusting a process or adjusting the parameters of e.g. an EP signal).

Where in embodiments of the present disclosure reference is made to a "stimulation unit," reference is made to a device that can provide electrical signals to an electrode for stimulating a cell (e.g. stimulating the formation of pores on the membrane of a cell) on an electrode. The stimulation unit includes a signal generator, which can provide an electroporation signal, e.g. a pulse generator, for example pulses and/or other signals such as pulse trains, continuous signals, pulses for impedance measurement and monitoring, etc. The stimulation unit may comprise a controlling element, such as a controller, or it may be connectable to an external controlling element. The controlling element may be configured to control the stimulation unit so it generates signals to measure impedance and/or to provide pores on the cellular membrane of a type of cell. For example, the controlling element may include a memory, lookup table or the like, or be connectable to an external memory. The memory may store predetermined signal parameters.

The present disclosure relates to a method and device for electroporation of cells. The cells are in contact with, e.g. attached to, an electrode, for example to an electrode with an area adapted to receive a cell, e.g. a single cell. A plurality of cells can be in contact with the electrodes of a micro-electrode array (MEA) which may comprise electrodes with a size suitable for accepting one cell, for example smaller than the cell of interest. For example, the cells of interest may be adherent cells, and in that case the surface of the electrode may be hydrophilic to enhance cell contact.

The control of the attachment can be done with markers, but these can influence the properties of the cell. Electroporation (EP) can be used to provide cargo (nucleic acid, proteins, etc.) to the cell. However, it is not easy to detect whether a cell has been sufficiently permeabilized so that transfection has taken place. On the other hand, the EP procedure should not induce irreparable damage such as cell death. The present disclosure provides a highly flexible combination of impedance sensing (electrical impedance measurement, e.g. electrical impedance spectroscopy (EIS)), with electroporation (EP). The process of electroporation will be explained with reference to FIG. 1 to FIG. 5.

FIG. 1 shows a graph of impedance as a function of time for a cell on an electrode. The graph is divided in four parts A, B, C, and D, each corresponding to a different stage of impedance spectroscopy (IS) and of electroporation. These situations of a cell in each of these stages is shown in FIG. 2 to FIG. 5.

Before electroporation, an initial measurement of impedance (for example, EIS, for example single frequency monitoring, etc.) yields data on cell-electrode contact and cell status. The initial impedance monitoring corresponds to the region A in FIG. 1, where the absolute value of the impedance is shown as a constant. The signal provided to measure impedance is adapted to avoid affecting the membrane structure. For example, it is not intense and/or lasting enough to produce electroporation. In some embodiments, this information can be used to detect presence of a cell, to estimate the adhesion of the cell to the electrode, and/or to prepare an optimized electrical signal.

Figure 2:
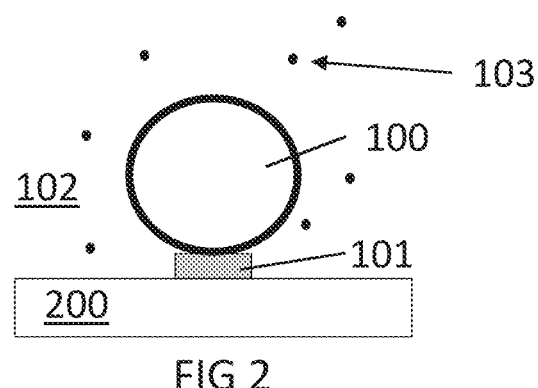
FIG. 2 is a representation of an electrode with a cell surrounded by a medium including cargo to be introduced within the cell, according to an example.

The situation of the cell corresponds to FIG. 2, where one cell 100 rests on an electrode 101. FIG. 2 to FIG. 5 shows four stages of a particular embodiment wherein electroporation is used for cell transfection, so the cell 100 is immersed in a medium 102 including cargo 103 (e.g. cellular material, e.g. proteins, e.g. nucleic acid material).

Figure 3:
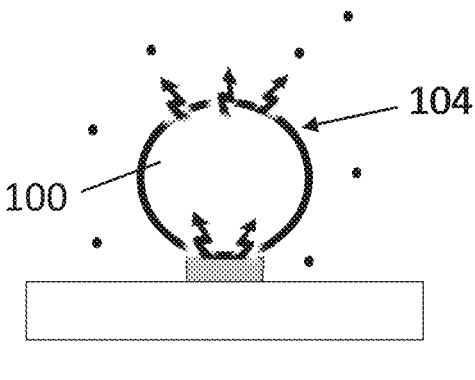
FIG. 3 is a representation of an electrode with a cell receiving an electrical signal through the electrode, which causes the formation of pores on the cellular membrane during electroporation, according to an example.

After measuring the impedance (e.g. monitoring), an EP signal is applied for producing pores 104 on the cell membrane (effectively "breaking" the membrane), see FIG. 3. Due to the formation of pores, the conductivity of the membrane changes which causes a change of impedance in the cell-electrode system. Also due to the pores, the membrane becomes permeable. Hence, membrane permeation can be detected as a dip in the values of the measured impedance. This dip is identified as region B in FIG. 1 caused by the EP. The amplitude of the dip (or drop) may be used to obtain information on the extent of the electroporation outcome: a large dip of impedance would indicate formation of pores which are large enough, and for a time long enough, to allow transfection, to allow the cargo to be successfully delivered.

Figures 4, 5, 6, 7:
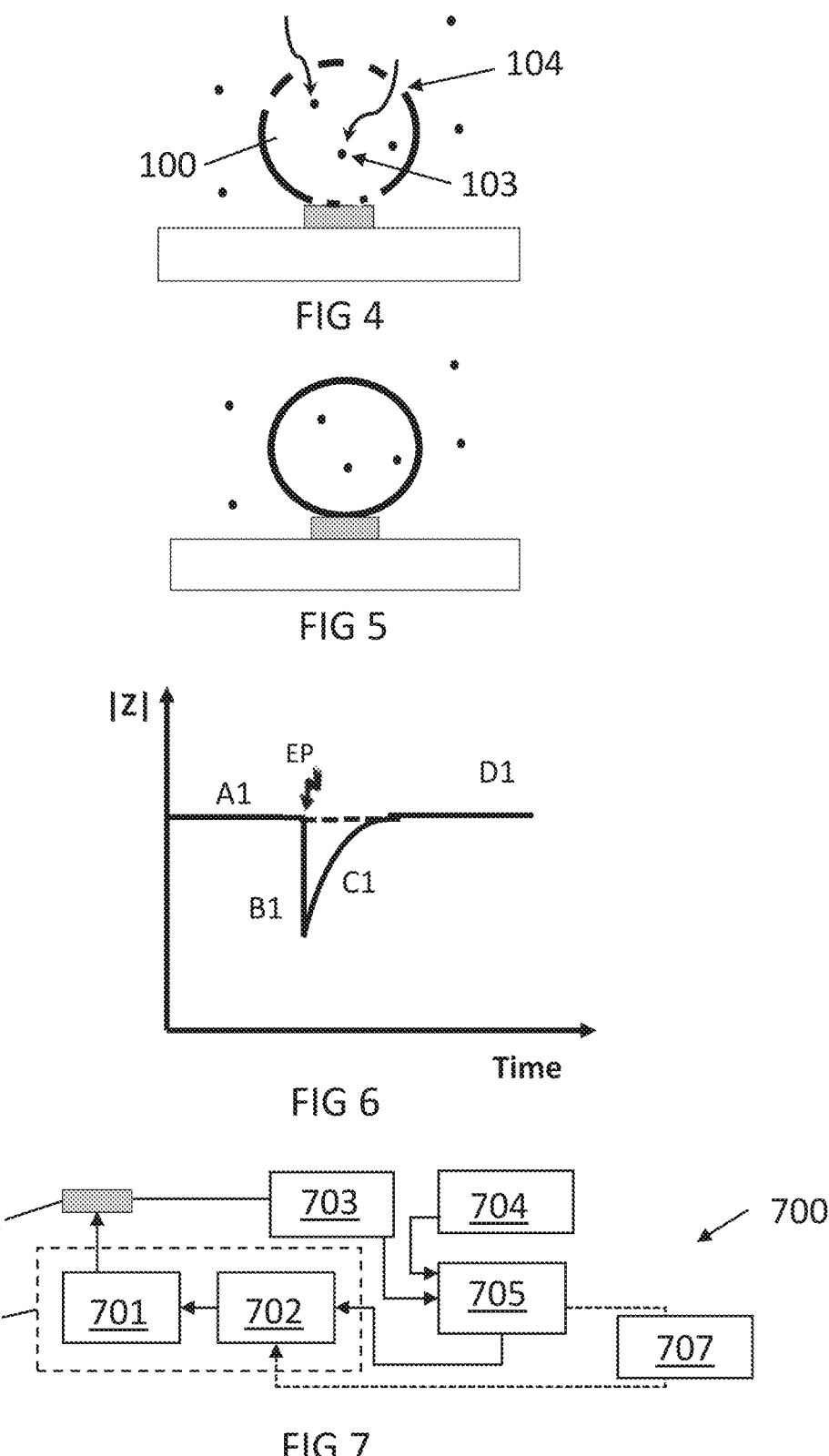
FIG. 4 is a representation of an electrode with a cell including pores produced by electroporation, according to an example. Cargo surrounding the cell enters the cell through these pores formed in the membrane, according to an example.
FIG. 5 is a representation of an electrode with a cell where pores have closed and cargo has been introduced in the cell, according to an example.
FIG. 6 is a graph of impedance as a function of time for a cell on an electrode showing four different stages of the impedance monitoring during electroporation in a failed transfection experiment, according to an example.
FIG. 7 is a representation of an electrode unit for producing electroporation including impedance measurement, according to an example.

The delivery is explained with reference to FIG. 4, showing the pores 104 and cargo 103 entering the cell 100 through them. Cell recovery takes place, and pores start closing. Hence, impedance measurement can be used to track the resealing of the pores, as shown in the relatively slow increase of the impedance (region C) of FIG. 1. An increase of the impedance values close to the initial, pre-application of the EP signal, indicates a healthy recovery.

Finally, FIG. 5 shows that the cell has survived the transfection, and long-term monitoring of impedance value may provide information of any transfection-induced status change, as differentiating changes may take place due to the cargo introduced. This is shown by the slow decline of the impedance in the last shown region D of the graph in FIG. 1 as compared to the original value (indicated by a dashed line).

This is the ideal case of single-cell transfection control through electroporation. The signal parameters are optimized for each cell (and electrode). Optimized electroporation signal parameters could be predetermined based on prior measurements at the single-cell level, or they may be obtained theoretically, by modelling, by experiments in literature. However, these predetermined parameters do not take into account external factors such as poor coupling between cell and electrode, or other uncontrollable and unknown factors that may affect electroporation and/or transfection. Thus, even when an electrode is in contact with a cell and an electroporation signal (EP signal) with predetermined parameters is applied to the electrode, there is no guarantee that electroporation will actually take place, or that the pores provided will be large enough and/or last long enough for transfection to take place.

FIG. 6 shows an exemplary impedance profile of transfection failure. The impedance spectroscopy shows an initial value A1 (which may be constant) and large enough to indicate presence of a cells on the electrode. Upon applying the EP signal, pores are produced on the cellular membrane and the impedance drops to a new value B1. However, the drop is not large enough, and the impedance starts increasing again (see the increasing curve C1), indicating closure of pores. The membrane is recovered completely and the impedance is back to the original values D1. There is no change in the impedance thereafter, e.g. no decrease. This indicates that the cell did not change, so it did not receive any cargo: transfection did not take place.

The disclosed systems and methods allow in-situ monitoring of the electroporation of cells, for example of individual (biological) cells, during the electroporation process, and repeating the EP signal, optionally adjusting the signal parameters to ensure proper electroporation for cellular transfection of cargo. At the same time, the systems and methods may provide lower cellular death rate during electroporation.

The systems and methods could abolish or reduce cytotoxicity and further increase efficiency. In some embodiments, the present disclosure includes an approach that allows tweaking of electroporation signal parameters. In some embodiments, after electroporation, single-cell level monitoring would offer insight into cell-to-cell variability in response to the transfection event. All the above features may be combined for performing transfection and phenotyping.

This present disclosure discloses comparing the measured impedance values with expected values stored in a memory. When the values are different, for example when the initial impedance is lower than expected, or when the change of impedance (or impedance drop) is smaller than predicted for that cell during electroporation, the electroporation process can be adapted dynamically. For example, the parameters of the EP signal are adapted accordingly if the initial impedance is lower than expected, to compensate for the low initial impedance. For example, if an impedance drop is lower than expected, a further signal can be applied, to ensure proper permeabilization of the cell membrane. On the other hand, some embodiments may allow adaptive learning. After cell death is detected, the predetermined values for electroporation experiments thereafter can be changed, for example by reconfiguring the stimulation unit.

Disclosed systems and methods can be used to deliver large signals, for example high amplitude pulses, and precisely transfect cells deposited atop the electrodes of a chip surface. Thanks to a wide range of tunable parameters, electrical stimulation of the cells can be optimized to obtain a high transfection efficiency and cell survival. Impedance measurement can be used to study cell morphology and function both at the level of the population and in individual cells. Impedance measurement can also be used to e.g. yield phenotypical data at the single-cell level and monitor the electroporation process, providing feedback on the electroporation efficiency and, in some embodiments, the ability to adapt the electrical signal, even during transfection experiments, based on a cell's phenotype and on the reaction to electrical stimulation.

Generally, there is no need of extra markers to detect cell attachment to the electrode. The impedance can be measured before electroporation to detect the presence of a cell. Optionally, the quality of electrode-cell attachment can be estimated.

In a first aspect, the present disclosure provides an electrode unit including at least one electrode with a shape, size, material, and preparation configured to form contact with a cell, for providing electrical signals to the cell, and also for measuring impedance at the interface between the electrode and the cell.

The electrode unit is configured to apply an EP signal which may be in accordance with a predetermined (e.g., optimized) value if the measured impedance is larger than an expected or threshold value stored in a memory. Otherwise an adjustment signal is generated and either a first EP signal has adapted parameters, or a further EP signal is sent after a first signal is sent. Mainly two cases can be defined: a) before the EP signal is applied, the initial impedance measurement does not reach the expected threshold, or b) during EP, where no transfection is predicted, due to a measured impedance drop less than expected.

FIG. 7 shows a schematic electrode unit 700. The unit includes an electrode 101. The electrode may be a microelectrode, with round or square shape, for example, with a size adapted to the size of the cell of interest. For example, it may have a size between 1 $\mu m^2$ (an area of 1 micrometer of width and length) and 400 $\mu m^2$, for example between 9 $\mu m^2$ and 100 $\mu m^2$. The electrode generally comprises material which is suitable for receiving cells. For example the material may be biocompatible, for example, the electrode may comprise a hydrophilic surface. The electrodes may comprise also a CMOS compatible material, for allowing chip integration in an array. In some embodiments, the electrodes may be coated with specific molecules or proteins. The exact composition of the electrode and/or of its coating, electrode size, etc. may be cell type specific, so for a cell type, different electrode sizes, coatings, and such can be used. Examples include materials with large charge injection capacity, such as Au and/or Pt, and/or CMOS compatible materials such as TiN. In some embodiments, the electrode unit is included in a biochip.

The electrode is connectable or connected to a stimulation unit 706. The stimulation unit is configured to provide electrical signals, for example, a continuous signal or alternating signals of adaptable frequency. It can be used for measuring impedance and for stimulating the formation of pores on the cellular membrane. In some embodiments where the electrode unit 700 is provided on a chip (e.g. monolithically integrated), a stimulation unit may be a microfabricated current and voltage source.

The stimulation unit 706 may comprise an electrical signal generator 701. For example, the signals can be provided as pulses of configurable duration and amplitude. The stimulation unit 706 may be configured to apply signals adapted to allow impedance monitoring (IM) of the cell and electrode, so that the measured impedance has enough intensity to be read by an impedance reading system, but without producing electroporation. For example, a signal to the cell may be adapted such that a constant impedance value can be measured without producing electroporation. The stimulation unit may be also configured to provide electroporation signals, with (optimized) predetermined parameters (e.g. amplitude or duration of pulses) to provide pores (e.g. for transfection), taking into account cell type and other experimental conditions, and which allow cell recovery. Thus, the stimulation unit 706 may be suitable to generate signals to measure impedance and signals to produce EP, such as a single pulse or multiple pulses, pulse trains, etc. For example, the signal generator 701 may be a pulse generator. The stimulation unit 706 may comprise a controlling element 702 such as a control unit, e.g. controller, processing unit or the like, to provide control of the actuation of the signal generator, and to adapt parameters if required, or even reconfigure these parameters. The controlling element 702 may be connected or connectable to the electrical signal generator 701 and to a memory, e.g. internal memory storing these predetermined values to measure impedance and to provide electroporation. Control may be digital. Other components such as buffers, signal converters, etc. can be included. The predetermined parameters may include continuous or alternate signal, frequency, amplitude, and parameters related to the shape of the signal (sinusoidal, square, including pulse duration, etc.).

The unit 700 includes an electronic impedance measurement device 703, e.g. an impedance sensor, configured to provide at least one type of impedance measurement (e.g. impedance spectroscopy, measurement of absolute impedance, etc.) of the impedance related to the cell on the electrode, in particular the impedance at the interface between electrode and cell. The impedance measurement device 703 detects for example whether there is a cell present on the electrode or not. The measurement can also give information of the quality of the contact between the cell and electrode.

The unit further comprises a memory 704 storing at least one predetermined value of an impedance parameter of a cell, in particular at least an impedance drop value which may serve as a minimum value indicative of cell membrane permeabilization, thus indicating formation of membrane pores suitable for providing transfection, the present disclosure not being limited thereto. For example, it may also comprise a threshold impedance value which serves as a minimum value indicative of good contact between the electrode and the cell.

The present disclosure enables comparing the measured values of impedance, in particular of impedance drop, with the predetermined values stored in memory 704. If the comparison gives a lower impedance value than expected, the process of electroporation can be adapted accordingly. For this, the electrode unit includes a comparing element 705 such as a comparator or the like, which can be configured to compare values stored in the memory with values measured with the impedance measurement device.

The comparing element 705 has access to the memory 704, e.g. the memory may be included in the comparing element 705, or may include connections to transmit information to the comparing element 705. The comparing element 705 is configured to receive signals from the impedance measurement device 703, e.g. through an input. It is also configured to produce a signal which triggers adjustment of the electroporation process. This adjustment signal, based on the result of the comparison, can be output and used as a part of the control of the stimulation unit 706. In particular, the adjustment signal is generated when the measured impedance drop value and the stored value are different by more than a predetermined threshold, to be determined by each particular case. In the present example, the adjustment signal is generated when the measured impedance is lower than the impedance value stored in the memory 704.

The present disclosure further provides feedback control of the stimulation unit based on the output of the comparing element 705. The comparing element 705 is connected or connectable to the stimulation unit 706, for providing at least adjustment signals from the comparing element 705 to the stimulation unit. In turn, the stimulation unit is configured to apply an electrical signal to the electrode 101 to provide electroporation, when an adjustment signal is generated by the comparing element.

In some embodiments, the adjustment signal prompts the stimulation unit to provide to the electrode with a further electrical signal which has corrected parameters, e.g. adapted parameters different from those predetermined pulse parameters, e.g. larger or smaller pulse amplitude, longer or shorter duration, or the like, based on the adjustment signal. These corrected parameters ensure that electroporation takes place, even if the measured impedance is very different than the expected impedance.

For example, the output of the comparing element 705 may be an input of the controlling element 702 which controls the signal generator 701. The controlling element 702 may be programmed to analyze the signal from the comparing element 705 and determine that a new EP signal is required, e.g. upon receiving an adjustment signal from the comparing element 705.

The feedback loop can be provided in operation, i.e. during use. If the first signal does not manage to provide enough permeabilization, the comparing element is configured to provide an adjustment signal to the stimulation unit 706, which can be adapted to provide the further EP signal even before the pores close completely with failed transfection (see portion D1 of FIG. 6). Typically the time for total cell recovery (the time it takes for all the pores to close) is within the order of minutes. Providing the further EP signal as soon as the impedance monitoring detects insufficient permeabilization increases the chances that the cell undergoes successful electroporation.

In such case the process of providing a new EP signal can be repeated, even before the pores close completely with failed transfection (see portion D1 of FIG. 6).

Optionally, the unit 700 may be adapted so that the parameters of the further electrical signal can be changed and adjusted, in particular the EP signal. For example, the number of pulses can be changed when the EP signal comprises multiple pulses. For example, the frequency of a train of pulses can be changed. The duration or amplitude, or both, can also be changed.

In some embodiments, the unit 700 may comprise a deciding element 707 which determines the parameters of the further electrical signal based on the comparison, based on the value of a function $f(Z_a, Z_b, \theta)$ including the measured and threshold drop values. The function may be for instance the difference between the impedance drop measured $Z_a-Z_b$ and the threshold impedance drop value $(\theta)$ stored in the memory.

If the measured impedance drop is close to the threshold, the EP signal will be decreased (shorter pulses, lower amplitude, less pulses on a pulse train, a combination thereof, etc.). In other words, a second threshold value strictly lower than the threshold value of the memory can be defined, either in the memory or in the deciding element. When the measured impedance drop is lower than the threshold drop value, but larger than a second threshold, the deciding element 707 is configured to adapt the EP signal of the further pulse so it is weaker than the previous pulse. Although the pores induced by the first electrical signal may not allow a good permeabilization, as the measured impedance drop is close to the threshold, the number and/or size of the pores is still significant. Thus, in order to reduce chances of killing the cell, the unit can be adapted to provide a weaker further electrical pulse to the cell during recovery (while the pores are closing) thus additionally saving time.

If the impedance drop is far from the threshold, the EP signal will be increased (longer pulses, more pulses, higher amplitude, a combination thereof, etc.). In other words, a third threshold value, lower than the second threshold value, can be defined. When the measured impedance drop is lower than the third threshold drop value, the deciding element 707 is configured to adapt the EP signal of the further pulse so it is stronger than the previous pulse. Thus, a stronger EP signal can be provided.

Optionally, a third threshold value can be defined, strictly lower than the second threshold. If the measured impedance drop has a value between the second and third threshold, the deciding element 707 is configured to adapt the EP signal of the further pulse so the EP signal can be kept the same, otherwise the EP signal can be increased as before.

In some embodiments, the comparing element 705 may comprise an operational amplifier with selectable references (e.g. references stored in memory) and with an output interpretable by the stimulation unit 706 (e.g. by the controlling element 702). In some embodiments, the comparing element 705 may comprise a unit programmed to provide digital comparison, which can be more versatile. Such unit may also comprise the memory 704, thus allowing for a more compact device. In some embodiments, the deciding element 707 and the comparing element 705 may be integrated in the same unit. In some embodiments, the controlling element 702 and the deciding element 707 are integrated in the same unit, and the comparing element 705 is adapted to send the result of the comparison to the deciding element 707 of the controlling element 702. In some embodiments, the memory, comparing element, and deciding element may be implemented in a single module, for example digitally in a processing unit which receives input from the impedance sensor and provides signals to the controlling element 702 for controlling the parameters of the signal (e.g. amplitude/duration of pulse, number of pulses, etc.).

In some embodiments, the unit may be adapted so that the impedance of the cell-electrode system is measured before electroporation, and if the value is lower than expected for that cell, to tune or adapt the parameters of the signal to yield permeabilization. For example, the memory 704 may also store an impedance threshold (initial impedance threshold value), the comparing element 705 may be configured to provide an adaptation signal if the measured initial impedance value is lower than expected (i.e. lower than the initial impedance threshold value). Finally, the stimulation unit may be configured to provide the stimulating electrical signal with the predetermined parameters, or upon receiving the adaptation signal, to provide the electrical signal with parameters such that a stronger signal can be provided, for example by increasing the parameters (duration, amplitude) of the signal being a pulse, or increasing the number of pulses of a pulse train, to a higher value than the predetermined or theoretical values required to produce electroporation on that cell.

The electrode unit may comprise other components such as buffers, signal conversion elements, etc. which may be functionally linked with the comparing element 705, memory, impedance measurement device, or the like.

Thus, the present disclosure provides a combination of electroporation and impedance measurement for single-cell electroporation, allowing for adjusting parameters of the stimulation signal, yielding electroporation with reduced or no risk of cell death.

Several different types of impedance measurement can be performed. The skilled person can choose the appropriate impedance measurement taking into account the type of experiment, type of cell, setup, etc. For example, fixed frequency can be used. For example, impedance monitoring can be done by probing single cells. This can be done before applying the electroporation pulse, during the pulse, and afterwards for monitoring recovery. The monitoring may be provided so a fixed or constant impedance is measured. For example, a pulsed AC signal can have a frequency between 10 Hz and 1 MHz, while sensing the impedance.

Figure 8:
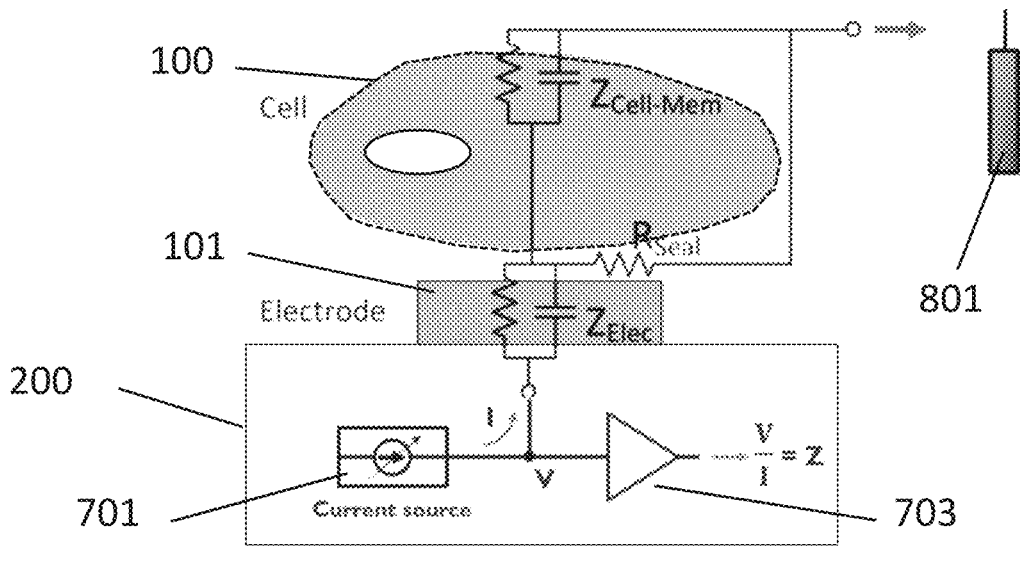
FIG. 8 is a representation of an electrode unit with a cell on top and a representation of the equivalent electric circuit formed by the cell-electrode system, according to an example.

FIG. 8 shows an electrode 101 with a variable current source acting as signal generator 701 and an impedance measurement device 703. A counter electrode 801 may be in contact with the medium. Some or all of these elements may be provided on a substrate 200 as shown in FIG. 2, e.g. an integrated substrate suitable for biosensing analysis and e.g. including microelectronic components and connections to provide the pulses and/or extract the signals. For example it may be a CMOS substrate, as shown in FIG. 8, and it may comprise a monolithic circuit. On top of the electrode 101 a cell 100 is shown. The cell 100 and electrode 101 form an impedance circuit. The equivalent circuit is shown on the image, including the impedance of the electrode $Z_{Elec}$ and the impedance of the cell-membrane system $Z_{Cell\text{-}Mem}$ in series, and the seal (or paracellular) resistance $R_{Seal}$. The total impedance of the electrode-cell system is measured by measuring the current and the voltage. If the impedance coincides with $Z_{Elec}$, it can be assumed that there is no cell present on the electrode. The quality of the contact can be also estimated, by comparing the measurement with typical values for the type and size of electrode and the type of cell.

Figure 9:
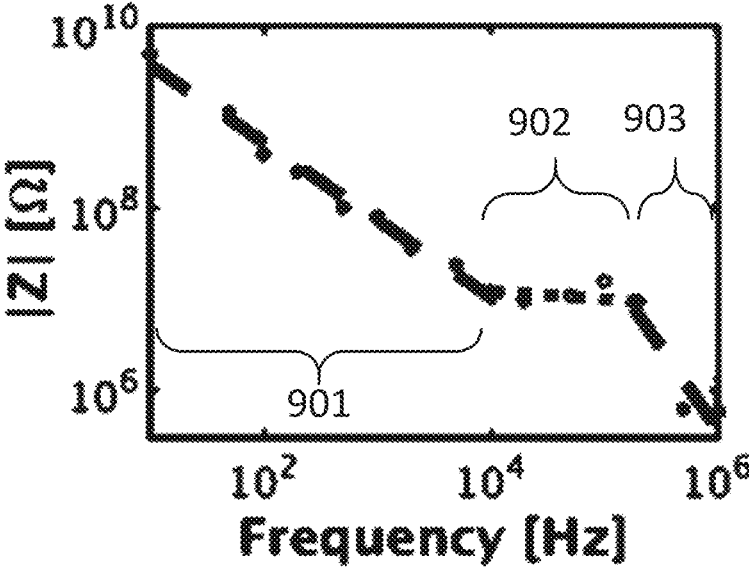
FIG. 9 is a graph of impedance as a function of frequency of an electrical signal for monitoring impedance, according to an example.

The impedance can be measured for a range of frequencies, as shown in the diagram of impedance vs frequency of FIG. 9. The data was adapted from experimental data from Mora Lopez et al, *ISSCC.* 2018, *Advanced Biomedical Systems*. Data was obtained experimentally and recorded on cardiomyocytes.

For an exemplary type of cell, the range 901 lower than 10 kHz gives information regarding electrode impedance. The range 902 between 10 kHz and 100 kHz gives information regarding the sealing resistance, or in other words, the resistance of the cellular membrane. This value drops when pores are formed, so this range of frequencies can be used to monitor pore formation. The range 903 with higher frequencies give information regarding transcellular impedance. Many cell types show a similar pattern, although the particular values (e.g. values of the plateau at mid-frequencies, shoulder value, etc.) may differ between different types of cells.

The electronic unit may include learning capability. For example, the stimulation unit may be configured to update or reconfigure the predetermined pulse parameters in case of cell death, for further experiments. Electricity may cause cell death via a number of different mechanisms (destruction of the membrane, etc.) and it usually happens due to use of an excessive value of some of the parameters of the pulse (e.g. pulse amplitude, duration, etc.). If cell death is detected, the controlling element 702 may be reconfigured so the signal generator 701 provides in further experiments a weaker signal, e.g. a pulse with lower values of e.g. amplitude, or less pulses of a pulse train, effectively reducing the predetermined values to safer levels. For example, the predetermined parameters of the pulse stored in the memory of the stimulation unit can be updated.

In a second aspect, the present disclosure provides an electrode array, where the electrode unit of embodiments of the first aspect of the present disclosure comprises a plurality of electrodes. Each electrode may comprise a generator, a memory, a comparing element, and channels for interchanging signals between these elements. In other embodiments a plurality of electrodes may share some of the elements such as the comparing element, the memory, and/or generator. A multiplexer, buffer, etc. may be included. The electrode array of embodiments of the second aspect of the present disclosure, in some cases, can circumvent the disadvantages of bulk electroporation (e.g. low efficiency, high cytotoxicity, incompatibility with adherent cells and no single cell addressability) by providing both electrical stimulation and impedance monitoring abilities. Impedance measurement and monitoring may be performed at multiple time points in the electroporation process. This allows fine-tuning with a feedback loop the electrical stimuli sent to the cells to achieve high transfection and low cytotoxicity.

In some embodiments, the electrode array may be a microelectrode array (MEA), for example a CMOS-based MEA, which may include thousands (e.g. over 16,000) of densely spaced, individually addressable, subcellular-sized electrodes. Single cell addressability can be enabled thanks to the small size of the electrode of the MEA. In some embodiments, the array additionally allows electrical impedance spectroscopy (EIS) for single-cell monitoring.

In some embodiments, the array of electrode units may be modular and include an electrode platform, e.g. a passive MEA, including an electrode array, connections or inputs to an impedance measurement and/or impedance spectroscopy unit, and a stimulation unit adapted to provide an electrical signal to produce electroporation (EP signal), e.g. comprising a pulse generator, to which the array of electrodes may connect and disconnect, e.g. physically remove, while at least some of the rest of the elements may form a single unit.

In some embodiments, the present disclosure provides a cell interfacing device (CID) and a chip comprising electrodes, e.g. an MEA, which can be controlled by the CID. The chip may be a disposable chip. Some elements of the electrode unit such as the stimulation unit, memory, comparators, etc. may be implemented in the CID which is connectable to the chip. The CID may comprise control software and/or hardware for controlling the operation of the electrodes (monitoring, etc.) and/or of the MEA of the chip. For example, the CID may be (re)programmable for selecting signal parameters for the electrode unit. For example, in FIG. 7, all elements (optionally except for the electrode 101, which may be in a disposable chip) may be integrated in a CID. In some embodiments, the CID may comprise microfluidic elements for allowing cell interfacing, e.g. cell interaction such as stimulation, monitoring and the like.

In a third aspect, the present disclosure provides a method of generating pores on cellular membranes of single cells. It can be used for electroporation of a biological cell during, for example, transfection.

The method comprises measuring impedance (e.g. electric impedance spectroscopy, e.g. impedance monitoring), comparing the measurements with stored predetermined values and, depending on the outcome, adapting the electroporation process if appropriate. Embodiments of the device of the first aspect can be used to carry out embodiments of the method of the present disclosure.

The method comprises applying an EP signal and measuring the impedance drop value, and if the drop and the threshold drop value are different by more than a predetermined amount or threshold, to be determined by each particular case. In the present example, the adjustment signal is generated when the measured impedance is lower than the predetermined drop threshold value. In that case, a further EP signal is applied.

Optionally, if the initial impedance (before EP) is lower than a predetermined initial threshold, an initial adjustment signal is generated, and the EP signal is increased.

Optionally, if the impedance measured after EP pulse is consistently low, then the EP signal for future experiments is lowered.

Figure 10:
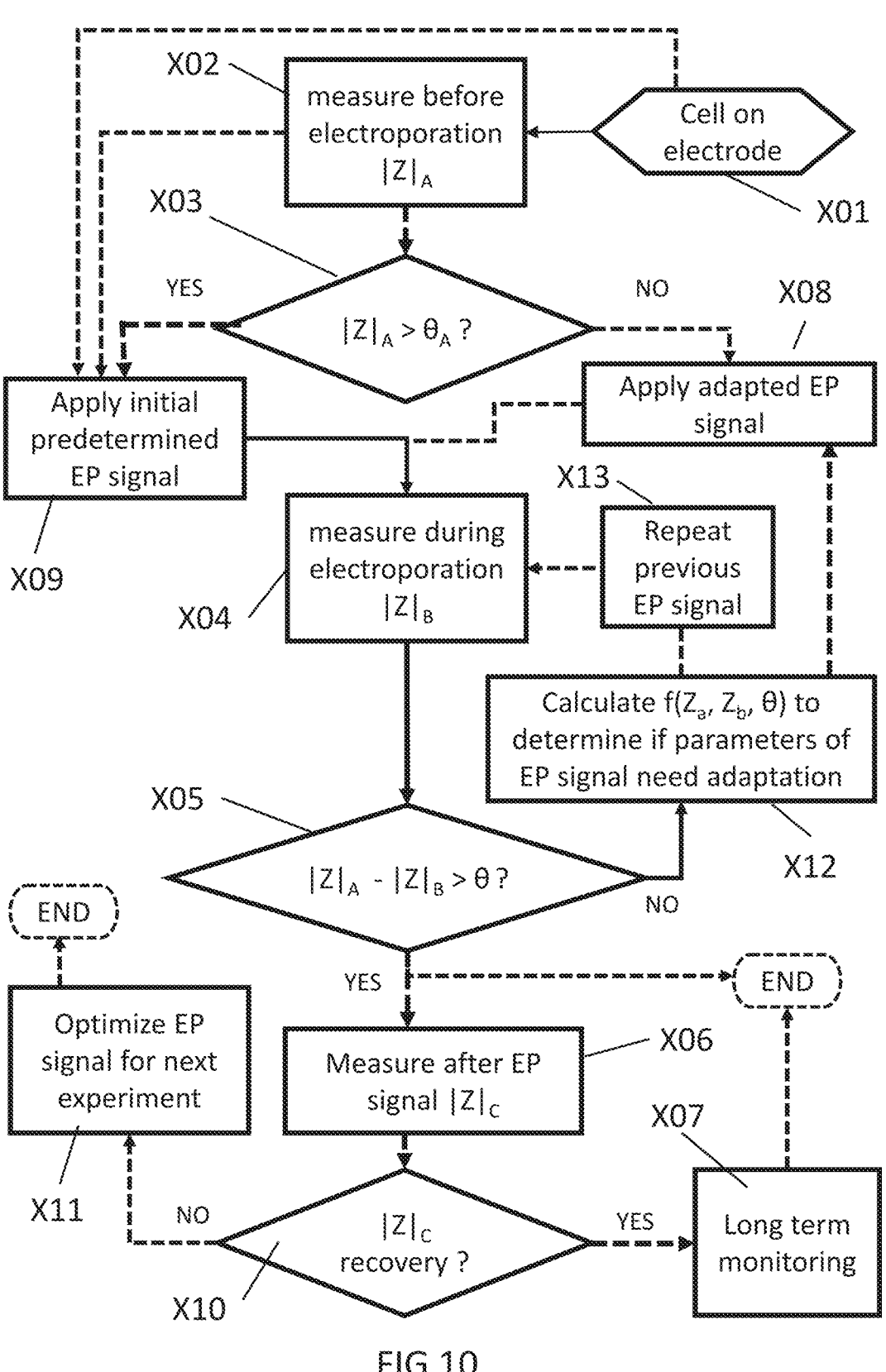
FIG. 10 is a flowchart showing steps of a method for electroporation, according to an example.

FIG. 10 is a flowchart showing steps of embodiments of the present method. As a preparation step, a cell is provided X01 on an electrode.

Impedance measurement can be provided X02 before electroporation to, for example, indicate the presence of a cell on the electrode. For example, a sinusoidal signal wave with a frequency between 10 Hz and 100 kHz, for example between 10 kHz and 100 kHz, with a predetermined amplitude, may be used to monitor membrane impedance. The intensity and voltage provided through the electrode-cell system can be used to obtain the impedance ($Z=V/I$). For instance, EIS can be provided by providing a signal modulated with a frequency, causing a variation of impedance on the cell-electrode system with a characteristic signature that can be picked up by EIS. Thus, it can be used to provide information concerning the phenotype of the cell on top of the electrode. Impedance measurement can be used before, during, and after electroporation to enhance its efficiency. In some embodiments, it may reduce the toxicity of the process. The initial impedance measurement may also provide information about the strength of the electrical contact between the two. As different cell types have different sensitivities to electroporation, and weaker cell-electrode coupling usually requires stronger pulses to yield successful transfection, initial impedance measurements can allow preparing a pre-optimised electrical stimulation and tailor it for each type of cell.

For example, an initial value of the impedance can be measured and compared to a predetermined impedance value which indicates good attachment and contact of a predetermined cell to an electrode. This predetermined impedance value or threshold value $\theta_A$ (theta-sub-A) may be stored in a memory 704 (FIG. 7) for the particular target cell. For the optimization, both the initial measured impedance value and the threshold value $\theta_A$ can be compared X03 and the parameters can be adapted before applying the pore-inducing stimulation.

Then, electroporation is induced by applying an EP signal. A first signal is sent X08, X09 that starts electroporation. The used EP signal parameters may be the predetermined parameters, or they may be parameters that have been adapted in accordance with the comparison between the expected initial impedance value and the measured impedance value.

During electroporation, the impedance (e.g. EIS, the disclosure not being limited thereto) is measured X04 to monitor the formation of pores on the plasma membrane of the cell and gives a measure of the extent of the membrane permeation. In the event of a failed or suboptimal electroporation that would lead to weak or no transfection, a new electrical signal will be applied X08, X13. The parameters of the signal may be the same as the first signal, or they may be adapted in accordance with the difference between a predetermined threshold drop value and the measured drop value. The process is repeated until satisfactory electroporation of the plasma membrane occurs. This step-by-step, feedback-controlled electroporation ensures that the cells are always stimulated with an adequate pulse, while avoiding over-exposure to electrical currents.

When the impedance measurements allows predicting successful electroporation, impedance ($Z_C$) is measured X06, e.g. for a period of time, to monitor the resealing of the membrane pores. Increasing impedance shows cell recovery and further survival (see increasing portion C, C1 of FIG. 1 and FIG. 6). Furthermore, long term changes of impedance (see final portion D of FIG. 1) can be traced to changes in cell properties, such as those occurring during a cell differentiation event caused by gene delivery.

In some embodiments of the present disclosure, a correlation is performed with the initial impedance measurements, the electrical pulses sent, and the cell recovery. This correlation helps further optimize the electroporation and monitoring process. It provides X07 a long-term feedback loop in which the system can learn from its experiences and be adapted in the next experiments.

The process flow chart of the closed-loop single cell electroporation in FIG. 8 will be now explained in more detail. The step of providing X01 a cell on an electrode may comprise for example placing a cell on top of the electrode, possibly providing a single cell to a single electrode. For example, a plurality of cells may be provided to an array of electrodes, so that each electrode may comprise one cell. Not all electrodes of the array might comprise a cell. For example, the cells may statistically distribute over the electrodes, so a plurality of electrodes may not receive any cell. This can be detected by measuring impedance, for example in a separate preparation step, or by performing X02 impedance measurement. Those electrodes in the array that do not include a cell do not need to be powered for electroporation, thereby saving energy and reducing the presence of statistically irrelevant data.

The step of performing X02 impedance measurement may comprise providing a signal on the electrode with characteristics such that impedance value of the cell-electrode is measured, without providing pores on the membrane. This can be done by providing an AC signal at a given frequency. Alternatively, multiple frequencies can be swept within a range, e.g. between 10 Hz and 1 MHz. Other methods known in the art can be used, for example a continuous signal. For example, a single DC pulse can be submitted (a square pulse, lasting a few ms) to the electrode while recording the resulting voltage transient. The transient can be used to estimate the impedance of the system. For example, EIS can be performed. In some embodiments of the present disclosure, "impedance value" or "value of impedance" refer to the impedance magnitude, for example its absolute value, i.e. the value without considering the sign.

The measured impedance value $Z_A$ before electroporation is compared to the threshold value $\theta_A$ explained earlier, and which is stored in the memory 704. This predetermined value indicates whether there is a cell on the electrode or not, as well as the quality of the coupling cell-electrode, so it depends on both the type of electrode and the type of cell. The threshold value stored in the memory 704 may be obtained for the cell beforehand, from models, simulations, known parameters from literature and/or previous tests, for example. Comparison can be done with the absolute value of the impedance.

If a cell is detected on the electrode, after initial impedance measurement, a first EP signal is sent to produce electroporation. The stimulation unit uses either predetermined parameters, thus providing X09 a first signal with predetermined parameters, or with adapted parameters, thus providing X08 a stronger signal, e.g. stronger or longer pulse, more pulses in a multiple-pulse signal, etc., depending on the results of the comparison of $\theta_A$ with $Z_A$.

In the case of good cell-electrode contact, the case is similar as the ideal case shown in FIG. 1. High initial impedance (absolute value $|Z|_A$) indicates strong cell-electrode coupling and predicts good electroporation outcome. After EP, impedance drops drastically, showing successful cell permeation. This provides proper cargo delivery. Impedance increases to initial values, showing pore resealing and cell recovery. The final portion D with slow changes in impedance values indicates long term survival of the cell and transfection-induced phenotype changes. If the comparison shows that the measured impedance is not lower than the threshold value, then the comparing element may send a signal accordingly (or not send any signal) to the controlling element 702 so a pulse with predetermined parameters can be used X09, instead of an adapted pulse.

Figure 11:
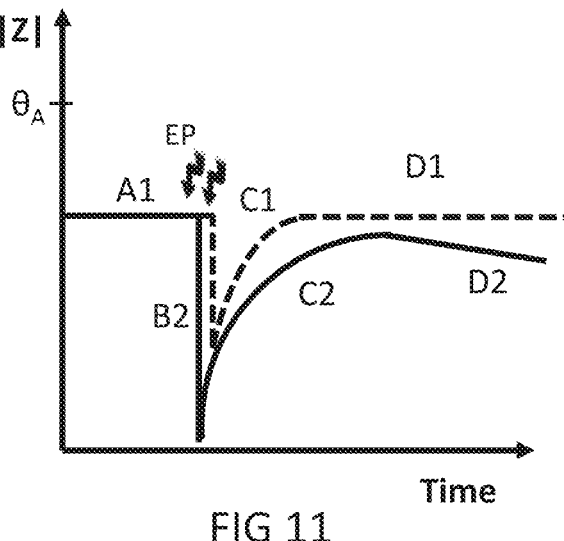
FIG. 11 is a graph of impedance as a function of time for a cell on an electrode showing four different stage of impedance measurements during electroporation for a case of failure of transfection due to insufficient contact between the cell and electrode, and the case of successful transfection even if the contact is insufficient, according to an example.

In the case of poor cell-electrode contact, the impedance value $|Z|_A$ is lower than the threshold value $\theta_A$, as shown in the graph of FIG. 6 and FIG. 11 (dashed line). The comparing element provides a signal to the controlling element 702 for adjusting the parameters of the electroporation pulse to be used. The adapted or "corrected" EP signal may be stronger than the predetermined signal for the cell, and/or it may be longer pulse, or the like. For example, as a response to the detection of a lower impedance, a "corrected,", e.g. stronger, pulse is sent X08, the predetermined parameters of the pulse (e.g. duration, amplitude, etc.) being adapted to account and compensate for the reduced (electrical) coupling between the cell and electrode. This is shown with the solid line B2 of FIG. 11. Additionally or alternatively, frequency of pulses in an EP pulse train can be tuned.

Due to EP, impedance drops drastically, showing successful cell permeation and anticipating cargo delivery. As before, the cell shows cellular survival and phenotype changes by a slow change of impedance. If a pulse with predetermined parameters was sent, the cell would not have been sufficiently electroporated (dashed line), because the predetermined parameters are obtained under the (ideal) condition that there is a good electrode-cell adhesion. It would show the same curve shape as the one in FIG. 6. Poor cargo delivery would take place, and fast increase of impedance would be measured indicating fast pore resealing, with long term survival and constant impedance values (possibly similar to the initial pre-pulse values) indicating no transfection-induced phenotype changes.

During the electroporation, impedance or parameters related to impedance are monitored, e.g. measuring X04 the impedance for a period of time. Monitoring allows for predicting that no transfection took place by comparing X05 the impedance behavior before cell recovery with the expected value. In particular, the minimum impedance value ZB attained before recovery can be measured. The measured impedance value before and after electroporation provides an impedance drop value (e.g. $|Z|_A - |Z|_B$) which can be compared X05 with a threshold drop value $\theta$ stored in a memory. As before, this predetermined threshold drop value may have been obtained by modelling, theoretically, from literature, etc. In theory, the lower impedance value obtained after electroporation could also or instead be used to detect whether electroporation took place and the amount thereof. The absolute post-electroporation impedance value $|Z|_B$ might not reach the impedance value of the bare electrode. However, in practice, calculation and comparison of the drop value is generally preferred, as the drop is less sensitive to the variability intrinsic of cell-electrode contact and to differences between electrodes due to manufacturing variability.

In the case of an incomplete electroporation, the drop of the impedance value will be smaller than the case in which the electroporation was sufficient (e.g. sufficient to provide effective transfection), so the measured impedance drop value $|Z|_A - |Z|_B$ will be smaller than a lower threshold value $\theta$. This means that not enough electroporation has been attained, so probably transfection will not take place. Thus, an adjustment signal is provided by the comparing element to the controlling element or deciding element so a second or, more in general, further electrical signal is sent X08, X13.

In embodiments of the present disclosure, it is not necessary to spend time checking whether the values of impedance return to the original values after cell recovery when the insufficient drop is detected. In this case, it can be predicted that insufficient transfection will occur, so it is safe to assume the impedance will go back to the initial, pre-electroporation value. The further pulse (or in other words, the pulse adapted to ensure electroporation after detecting suboptimal conditions for it) can be applied again even during membrane closure and recovery, thus saving time.

Figure 12:
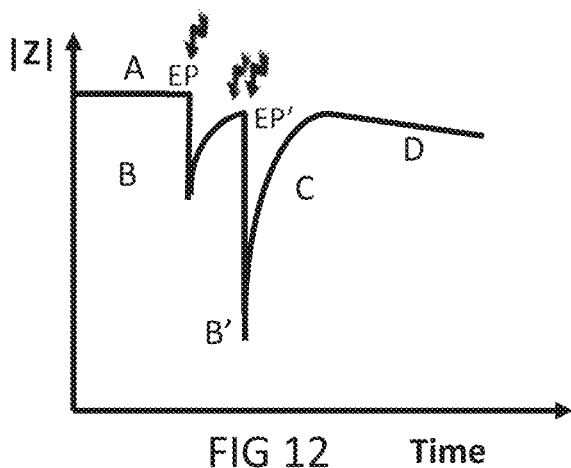
FIG. 12 is a graph of impedance as a function of time for a cell on an electrode where the impedance drop is less than expected during electroporation, so the membrane starts closing the pores with no time for cargo to enter the cells. A second signal is sent with adapted characteristics to open pores again and for longer time to effectuate transfection, according to an example.

This particular case is shown in FIG. 12. In this example, portion A shows a high initial impedance in portion A. This indicates strong cell-electrode coupling and predicts good electroporation outcome. After EP, for unknown reasons, impedance drops slightly only, and the drop value $|Z|_A - |Z|_B$ is lower than expected, showing poor cell permeation (thus, poor cargo delivery). The cell starts recovery, which is monitored.

Upon starting recovery, the impedance starts increasing. The measured drop value of the impedance is compared with the expected threshold drop value $\theta$ stored in the memory 704. Because the measured drop value is, for example, smaller than the threshold drop value $\theta$, the comparing element 705 generates an adjustment signal which is sent to the controlling element 702 of the stimulating unit 706 (or to the deciding element 707).

As a result, a further EP signal is submitted, and a new minimum value of the impedance $|Z|_{B3}$ is measured during the monitoring. The drastic impedance drop shows successful cell permeation which anticipates successful cargo delivery. The monitoring of impedance continues but no new pulse is required. The impedance increases to initial values (portion C3), showing pore resealing and cell recovery. Long term survival of the cell is shown in the last portion D3. Changes in impedance values indicate transfection-induced phenotype changes, which shows successful transfection as explained earlier.

The further signal, as explained earlier, may be stronger, the same, or weaker than the previous signal which caused the measured drop. A function f can be calculated X12 based on the threshold impedance drop value $\theta$ and the measured drop value $|Z|_A - |Z|_B$. The choice of parameters may be based on the value of this function. The function may be a ratio, weighted function, or any other which can be optimized or enhanced based on the system cell-electrode, data analysis, etc. For example, the function may be a difference between the measured drop value $|Z|_A - |Z|_B$ and the threshold drop value $\theta$. As explained earlier, a further threshold can be predetermined, so if the measured drop is smaller than expected but greater than this second threshold drop value, the signal may be close to producing proper electroporation, so the parameters of the signal can be adapted X08 to provide a new weaker pulse, e.g. while the pores are closing, so the cell is not damaged. If the measured drop is larger, the signal may on the other hand be the same as before, or adapted X08 to be stronger. Alternatively, a third threshold drop value can be defined. If the measured drop is lower than this third threshold drop, the applied further EP signal may be adapted X08 to be stronger than the previous signal. If the measured drop falls between the second and third thresholds, the applied EP signal may be the same as the previous one, thus repeating X13 the parameters of the previous EP signal.

The decision or choice of parameters used for the further signal, as explained earlier, may be taken by a deciding element, which may be a program, a module, etc. and may be external or implemented together with e.g. the controlling element in a module.

It may happen that both the case of FIG. 11 and FIG. 12 occur, so a cell with low initial impedance value (indicating suboptimal cell-electrode contact) requires a stronger signal than the electrical signal with predetermined parameters, so the stimulation unit is adapted accordingly, but the impedance drop is not large enough, and upon detection of this smaller drop, the further signal is sent again. The feedback loop allows repetition until the drop is large enough.

Figure 13:
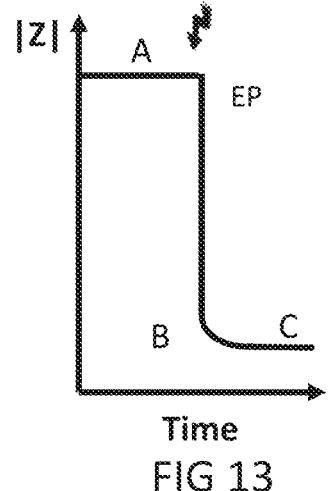
FIG. 13 is a graph of impedance as a function of time for a cell on an electrode showing cell death where there is no recovery of the cell membrane, according to an example.

Another possibility is that the EP signal causes electroporation to a deadly degree. This may happen due to an excessive strength of the EP signal, for example the pulse being too long, too intense, too powerful, too many pulses used or the like (due to e.g. using wrong settings for the type of cell, for example), or that the attachment threshold was set too high. This may cause the formed pores to not close on time or to become irreversible, damaging the membrane and triggering cell death. This is shown in FIG. 13, where after EP, steady low impedance values appear, which indicate cell death. There is no recovery, and the low impedance values show e.g. the impedance of the remains of the cell on the electrode. The cell did not recover from the pulse. This result will be considered in the next experiments, allowing tune down or adapting at least one parameter of the EP signal, for example of the predetermined parameters of the EP signal, or for the correction parameters used after detecting poor contact if cell death occurred after an initial adjustment signal was sent, or the like. Thus, the method enables updating and optimizing X11 the values of the parameters of the predetermined pulse (e.g. by updating or reconfiguring the stimulation unit, e.g. the controlling element 702, e.g. an internal memory storing these values, or even the deciding element 707) when the monitoring X10 of the impedance $Z_C$ of the impedance after the EP signal shows a continuously low value, with no recovery.

The steps of the method dealing with data treatment and comparison, signal generation, and transmission can be implemented by a control software, for example in a controlling element, external or internal, or by interconnected modules. The software may be implemented in a CID.

In an aspect, the present disclosure comprises a software product adapted to perform the steps of the embodiments of the method when executed in an electrode unit, e.g. in a CID, e.g. at least the steps of applying a first electrical signal to produce electroporation, measuring the impedance drop value of the electrode in contact with the cell, comparing the measured impedance value or drop value with a predetermined value of impedance drop of the biological cell, and applying a further signal to the cell via the electrode to produce electroporation when the comparison results in a difference of more than a predetermined threshold.

It is to be noted that primary cells types may present substantial cell to cell variation so they may need different pulse profiles. The present disclosure allows taking this variation into account, thanks to the initial impedance measurement $Z_A$ and comparison with the threshold value.

Impedance monitoring can be used as a built-in control strategy and quality check for electroporation. It enables higher transfection efficiency and cell survival and opens transfection to both suspended and adherent cells, hard-to-transfect cells, and cells available in small quantities such as primary cells. Moreover, addressing single cells offers an unprecedented precision of impedance measurement and electroporation efficiency. The MEA platform of embodiments of the present disclosure also enables long term monitoring and tracking of single cells deposited atop its surface. It is a potential advantage over standard microfluidic devices, in which track of single cells is lost in a bulk population and that cannot process adherent cells. In addition, especially in primary cell types, substantial cell-to-cell variation exists which can be taken into account by providing distinct electrical pulse profiles for successful yet non-toxic pore formation on these individual cells of a same primary cell type.

The present disclosure enables a highly efficient single-cell transfection platform which can play a key role in in-vitro diagnostics, oncology, gene-therapy, or tissue engineering, among other applications. The closed-loop charge-balancing circuit described here is an electrical circuit element that makes sure the electrical pulse submitted to the electrode can be precisely controlled in amplitude and duration.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. An electrode unit comprising:

an electrode configured to contact a biological cell and provide a first electrical signal to the biological cell and configured for measuring (i) a first impedance of the electrode and the biological cell measured before providing the first electrical signal to the biological cell and (ii) a second impedance of the electrode and the biological cell measured after providing the first electrical signal to the biological cell;

a stimulation unit electrically connected to the electrode;

an impedance measurement device configured to measure the first impedance and the second impedance of the electrode and the biological cell contacting the electrode and configured to measure a third impedance of the electrode and the biological cell after measuring the second impedance; and a comparing element configured to make a determination of whether the first impedance is greater than a first predetermined threshold and configured to produce an adjustment value based on whether an impedance drop is greater than a second predetermined threshold, wherein the impedance drop is a difference between the first impedance and the second impedance, the stimulation unit being configured to apply, via the electrode, the first electrical signal based on the determination and a second electrical signal to the biological cell based on the adjustment value and configured to update the first electrical signal for future application to another biological cell based on whether the third impedance is greater than the second impedance by more than a third predetermined threshold.

2. The electrode unit of claim 1, wherein the electrode unit is configured to obtain the first impedance without causing electroporation.

3. The electrode unit of claim 1, wherein the stimulation unit is configured to strengthen the second electrical signal in response to the electrode unit determining that the first electrical signal has not generated electroporation.

4. The electrode unit of claim 1, wherein the comparing element is configured to produce the adjustment value if the impedance drop does not reach the second predetermined threshold, and wherein the stimulation unit is configured to provide the second electrical signal as soon as the adjustment value from the comparing element is received.

5. The electrode unit of claim 1, wherein the stimulation unit is configured to reduce an energy of the second electrical signal if the impedance measurement device does not detect an increase of the second impedance after applying the first electrical signal.

6. The electrode unit of claim 1, wherein the electrode is a microelectrode.

7. The electrode unit of claim 1, further comprising an electrode array that comprises the electrode.

8. A cell interfacing device comprising the electrode unit of claim 1.

9. The electrode unit of claim 1, wherein the first predetermined threshold indicates attachment and contact of the biological cell to the electrode.

10. The electrode unit of claim 1, wherein the stimulation unit is configured to apply the first electrical signal using parameters that are based on the first impedance.

11. A method of using the electrode unit of claim 1, the method comprising:

providing the biological cell on the electrode;

measuring the first impedance of the electrode and the biological cell;

thereafter applying the first electrical signal to the biological cell via the electrode using first parameters that are based on the first impedance;

measuring the impedance drop of the electrode in contact with the biological cell, the impedance drop occurring in response to the first electrical signal, wherein the impedance drop is the difference between (i) the first impedance of the electrode and the biological cell measured before applying the first electrical signal to the biological cell and (ii) the second impedance of the electrode and the biological cell measured after providing the first electrical signal to the biological cell;

identifying second parameters for the second electrical signal based on the impedance drop;

making the determination of whether the first impedance is greater than the first predetermined threshold;

producing the adjustment value based on whether the impedance drop is greater than the second predetermined threshold;

applying the second electrical signal based on the adjustment value to the biological cell via the electrode;

measuring the third impedance of the electrode and the biological cell after measuring the second impedance; and updating the first electrical signal for future application to another biological cell based on whether the third impedance is greater than the second impedance by more than a predetermined threshold.

12. The method of claim 11, wherein measuring the first impedance comprises measuring the first impedance without causing electroporation of the biological cell.

13. The method of claim 11, wherein measuring the first impedance comprises measuring the first impedance to be greater than a threshold impedance, the method further comprising identifying the first parameters for the first electrical signal based on the first impedance being greater than the threshold impedance, wherein applying the first electrical signal comprises applying the first electrical signal using the first parameters.

14. The method of claim 11, wherein measuring the first impedance comprises measuring the first impedance to be less than a threshold impedance, the method further comprising identifying the first parameters for the first electrical signal based on the first impedance being less than the threshold impedance, wherein applying the first electrical signal comprises applying the first electrical signal using the first parameters.

15. The method of claim 11, wherein measuring the impedance drop comprises measuring the impedance drop to be greater than a threshold impedance drop, the method further comprising identifying the second parameters for the second electrical signal based on the impedance drop being greater than the threshold impedance drop, wherein applying the second electrical signal comprises applying the second electrical signal using the second parameters associated with the impedance drop being greater than the threshold impedance drop.

16. The method of claim 11, wherein measuring the impedance drop comprises measuring the impedance drop to be less than a threshold impedance drop, the method further comprising identifying the second parameters for the second electrical signal based on the impedance drop being less than the threshold impedance drop, wherein applying the second electrical signal comprises applying the second electrical signal using the second parameters associated with the impedance drop being less than the threshold impedance drop.

17. The method of claim 11, further comprising:

applying a further electrical signal to the biological cell in response to determining that the first impedance differs from a predetermined value corresponding to the biological cell by more than a threshold amount.

18. The method of claim 11, further comprising:

applying a further electrical signal to the biological cell in response to determining that the first impedance is less than a threshold amount, wherein the further electrical signal is weaker than the second electrical signal.

19. The method of claim 11, wherein the electrode is a microelectrode.

* * * * *